United States Patent [19]
Broughton et al.

[11] Patent Number: 6,156,787
[45] Date of Patent: *Dec. 5, 2000

[54] SUBSTITUTED THIENLYCYCLOHEXANONE DERIVATIVES FOR ENHANCING COGNITION

[75] Inventors: Howard Barff Broughton, Harlow; Mark Stuart Chambers, Puckeridge, both of United Kingdom

[73] Assignee: Merck Sharp & Dohme Limited, Hoddesdon, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/296,753

[22] Filed: Apr. 22, 1999

[30] Foreign Application Priority Data

Apr. 23, 1998 [GB] United Kingdom ............... 9808665

[51] Int. Cl.$^7$ .......................... A61K 31/38; A61K 31/40; C07D 333/56; C07D 405/00

[52] U.S. Cl. .......................... 514/443; 514/422; 514/324; 514/253; 514/233.5; 514/212; 549/57; 549/44; 549/45; 548/525; 546/202; 544/374; 544/146; 540/596

[58] Field of Search ............... 549/57, 44, 45; 514/443, 442, 324, 253, 233.5, 212; 548/525; 546/202; 544/374, 146; 540/596

[56] References Cited

U.S. PATENT DOCUMENTS 5,587,486  12/1996  Nakagawa et al. ............... 548/448

FOREIGN PATENT DOCUMENTS

96/16954   6/1996  WIPO .
WO 98 18792  5/1998  WIPO .

OTHER PUBLICATIONS

Van Rhee et al, "Tetrahydrobenzothiophene Derivatives as a Novel Class of Adenosine Receptor Antagonists", J.Med. Chem., 1996, 39, 398–406.

Primary Examiner—Deborah C. Lambkin
Attorney, Agent, or Firm—Shu M. Lee; David L. Rose

[57] ABSTRACT

The present invention provides compounds of formula (I) or pharmaceutically acceptable salts thereof:

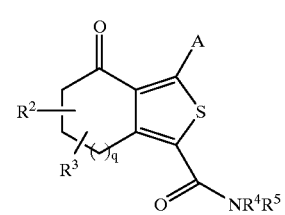

(I)

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^6$;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, each of which rings is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$ cycloalkyl group;

$R^4$ and $R^5$ are individually hydrogen, $C_{1-6}$alkyl, $C_{2-6}$alkenyl, $C_{2-6}$alkynyl or $C_{3-8}$cycloalkyl or $R^{12}$ and $R^{13}$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^6$ is hydrogen or $C_{1-6}$alkyl;

p is zero, 1 or 2; and q is 0, 1 or 2;

the preparation of these compounds, their use in enhancing cognition in disease states, particularly Alzheimer's disease, and methods of treatment using them.

7 Claims, No Drawings

SUBSTITUTED THIENLYCYCLOHEXANONE DERIVATIVES FOR ENHANCING COGNITION

The present invention relates to pharmaceutical compounds which are generally amide substituted thienylcyclohexanone derivatives and to their use in therapy. More particularly, this invention is concerned with substituted derivatives which are ligands for $GABA_A$ receptors, in particular for $GABA_A$ α5 receptors and are therefore useful in therapy particularly where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3 βγ2 subunits will possess desirable anxiolytic properties. The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the $GABA_A$ α5 receptor subtype.

WO-A-9616954 mentions three thienylcyclohexanone derivatives substituted by substituted arylaminocarbonyl on the thiophene ring as fungicides.

Van Rhee et al, *J. Med. Chem.*, 1996, 39, 398–406 discloses related compounds as adenosine receptor antagonists which differ in having an ester group on the thiophene ring.

The present invention provides a compound of formula (I) or a pharmaceutically acceptable salt thereof:

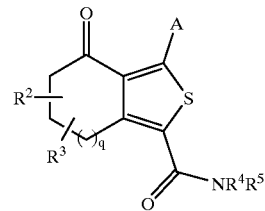

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^6$;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, each of which rings is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ and $R^5$ are individually hydrogen, $C_{1-6}$alkyl, $C_{2-6}$alkenyl, $C_{2-6}$alkynyl or $C_{3-8}$cycloalkyl or $R^4$ and $R^5$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^6$ is hydrogen or $C_{2-4}$alkyl;

p is zero, 1 or 2; and q is 0, 1 or 2.

$R^1$ is preferably $C_{1-6}$alkyl, $C_{2-6}$alkenyl or $C_{3-6}$cycloalkyl each of which is optionally substituted by amino, di($C_{1-6}$alkyl)amino, hydroxy, $C_{1-6}$alkoxy, $C_{1-6}$alkylaminocarbonyl or one, two or three halogen atoms; aryl or aryl$C_{1-6}$alkyl optionally substituted on the aryl ring by halogen, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, which ring is optionally substituted by halogen, $C_{1-6}$alkoxy, $C_{1-6}$alkylthio, aryl or $C_{1-6}$alkyl.

More preferably $R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or one, two or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio. In particular $R^1$ is $C_{1-6}$alkyl optionally substituted by one, two or three fluorine atoms, phenyl optionally substituted by fluorine or chlorine, or thiazole optionally substituted by $C_{1-4}$alkyl or fluorine.

A may be $S(O)_pR^1$.

When A is not $S(O)_pR^1$, $OR^1$ or $NR^1R^{14}$ it is preferably $C_{1-6}$alkyl, $C_{2-6}$alkenyl or $C_{3-6}$cycloalkyl.

When A is $OR^1$, $R^1$ is generally $C_{1-6}$alkyl optionally substituted by $C_{1-4}$alkoxy, $C_{3-6}$cycloalkyl or aryl, particularly aryl.

Particular embodiments of A are phenyl, cyclohexyl, 2-methylprop-1-enyl, methylthio, ethyl, isopropyl, propyl, cyclobutyl, but-3-enyl, cyclopropyl, methanesulphonyl, methyl, benzyl, methanesulphinyl, (1,1-dimethylethyl)thio, pentylthio, (4-methyl-1,2,4-triazol-3-yl)thio, hexylthio, benzylamino, (3-imidazol-1-ylpropyl)amino, (pyrid-2-yl) amino, 2-methylprop-1-yl, [3-(4-methylpiperazin-1-yl) propyl] amino, methylamino, (2-hydroxyethyl)amino, azetidin-1-yl, tert-butylamino, isopropylthio, (2-hydroxyethyl)thio, methoxy, dimethylamino, cyclobutoxy, phenoxy, butylthio, (3-chloropropyl)thio, (2-phenylethyl)thio, propylthio, (2-methylbutyl)thio, (2,2,2-trifluoroethyl)thio, (1-methylpropyl)thio, (4-chlorophenyl) thio, (3-fluorophenyl)thio, (4-acetylaminophenyl)thio, (4-methoxyphenyl)thio, (1-methylimidazol-2-yl)thio, (thiophen-2-yl)thio, (imidazol-2-yl)thio, (4-phenylthiazol-2-yl)thio, (1,2, 4-triazol-3-yl)thio, (5-methyl-1, 3, 4-thiadiazol-2-yl)thio, (5-methylthio-1,3, 4-thiadiazol-2-yl) thio, benzylthio, cyclopentylthio, (2-methylpropyl)thio, (furan-2-ylmethyl)thio, (2-hydroxy-1-methylpropyl)thio, (2,3-dihydroxypropyl)thio, (2-hydroxypropyl)thio, ((N-methylaminocarbonyl)methyl)thio, (pyrid-4-yl)thio, (pyrimidin-2-yl)thio, (thiazol-2-yl)thio, prop-2-enylthio, (pyrid-2-yl)thio, ethylthio, phenylthio, (N,N-dimethyl-2-aminoethyl)thio, (2-methoxyethyl)thio, (furan-2-ylmethyl) amino, (2-methylpropyl)amino, propylamino, (2-methoxyethyl)amino, cyclopropylamino, isopropylamino, ethylamino, cyclobutylamino and isopropoxy.

Preferred particular embodiments of A are phenylthio, ethylthio, thiazol-2-ylthio, methylthio, 1-(2,2,2-trifluoroethyl)thio, isopropylthio and phenoxy.

$R^2$ and $R^3$ are preferably independently chosen from hydrogen and methyl or are attached to the same carbon atom and together with that atom form a $C_{3-6}$cycloalkyl group, and are most preferably both methyl. Preferably $R^2$ and $R^3$ are geminal to each other, preferably at the 6-position, i.e. beta to the carbonyl group in formula I.

$R^4$ and $R^5$ are preferably independently hydrogen, $C_{1-4}$alkyl or $C_{3-6}$cycloalkyl or $R^4$ and $R^5$, together with the nitrogen atom to which they are attached, form a saturated 5 to 7-membered ring optionally containing an oxygen atom or a further nitrogen atom at the 4-position, the further nitrogen atom being unsubstituted or substituted with $C_{1-4}$alkyl. More particularly $R^4$ and $R^5$ are independently hydrogen, methyl or cyclohexyl or $R^4$ and $R^5$ together with the nitrogen atom to which they are attached form a piperidine, piperazine, hexamethyleneimine or morpholine ring, the further nitrogen atom in the piperazine ring being optionally substituted by methyl.

Particular embodiments of $NR^4R^5$ are pyrrolidine, N-methyl-N-cyclohexylamine, N,N-dimethylamine, morpholine, N-methylpiperazine and hexamethyleneimine.

$R^6$ is generally hydrogen or $C_{1-4}$alkyl and most preferably hydrogen.

p is preferably zero or two, most preferably zero.

q is preferably 1.

There is further provided a subclass of compounds of formula (I) according to the present invention wherein:

A is $S(O)_pR^1$ or $OR^1$;

$R^1$ is $C_{1-6}$alkyl optionally substituted by one, two or three fluorine atoms, phenyl optionally substituted by fluorine or chlorine, or thiazole optionally substituted by $C_{1-4}$alkyl or fluorine;

$R^2$ and $R^3$ are methyl;

$R^4$ and $R^5$ are independently hydrogen, methyl or cyclohexyl or $R^4$ and $R^5$ together with the nitrogen atom to which they are attached form a piperidine, piperazine, hexamethyleneimine or morpholine ring, the further nitrogen atom in the piperazine ring being optionally substituted by methyl;

p is zero or two; and q is one;

and the pharmaceutically acceptable salts thereof.

The preferred definitions of each substituent hereinbefore recited apply *mutatis mutandis* to this subclass.

Particular compounds illustrating the present invention are:

6,6-dimethyl-3-methylthio-1-(pyrrolidin-1-ylcarbonyl)-4, 5,6,7-tetrahydrobenzo [c]thiophen-4-one;

6,6-dimethyl-1-(dimethylaminocarbonyl)-3-methylthio-4,5,6,7-tetrahydrobenzo [c]thiophen-4-one;

6,6-dimethyl-1-[(methyl)cyclohexylaminocarbonyl]-3-methylthio-4,5,6,7-tetrahydrobenzo[c]thiophen-4-one;

6,6-dimethyl-3-phenylthio-1-(pyrrolidin-1-ylcarbonyl)-4, 5,6,7-tetrahydrobenzo[c]thiophen-4-one;

6,6-dimethyl-3-ethylthio-1-(pyrrolidin-1-ylcarbonyl)-4,5, 6,7-tetrahydrobenzo[c]thiophen-4-one;

6,6-dimethyl-1-(pyrrolidin-1-ylcarbonyl)-3-(thiazol-2-ylthio)-4,5,6,7-tetrahydrobenzo[c]thiophen-4-one;

6,6-dimethyl-1-(homopiperidin-1-ylcarbonyl)-3-methylthio-4,5,6,7-tetrahydrobenzo[c]thiophen-4-one;

6,6-dimethyl-1-(pyrrolidin-1-ylcarbonyl)-3-(2,2,2-trifluoroethylthio)-4,5,6,7-tetrahydrobenzo[c]thiophen-4-one;

6,6-dimethyl-3-isopropylthio-1-(pyrrolidin-1-ylcarbonyl)-4,5,6,7-tetrahydrobenzo[c]thiophen-4-one;

6,6-dimethyl-3-phenyloxy-1-(pyrrolidin-1-ylcarbonyl)-4,5,6,7-tetrahydrobenzo[c]thiophen-4-one;

6,6-dimethyl-3-methylthio-1-(morpholin-4-ylcarbonyl)-4,5,6,7-tetrahydrobenzo[c]thiophen-4-one;

6,6-dimethyl-1-(4-methylpiperazin-1-ylcarbonyl)-3-methylthio-4,5,6,7-tetrahydrobenzo[c]thiophen-4-one;

and the pharmaceutically acceptable salts thereof.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the $\alpha5$ subunit. In particular, they are desirably inverse agonists of the $\alpha5$ subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $\alpha2$ or $\alpha3$ subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha 5$ subunit, in particular for conditions requiring cognition enhancement such as Alzheimer's disease.

There is also disclosed a method of treatment or prevention of a condition associated with $GABA_A$ receptors containing the $\alpha 5$ subunit which comprises administering to a subject suffering from or prone to such a condition a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "$C_{1-4}$alkyl", "$C_{2-4}$alkenyl", "$C_{2-4}$alkynyl" and $C_{1-6}$alkoxy are to be construed in an analogous manner.

The expression "$C_{3-6}$cycloalkyl" includes cyclopropyl, cyclobutyl, cyclopentyl and cyclohexyl groups. "$C_{3-8}$cycloalkyl" and "$C_{5-7}$cycloalkyl" are to be construed analogously.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine, especially fluorine, chlorine and bromine.

The expression "aryl$C_{2-6}$alkyl" as used herein includes benzyl, phenylethyl, phenylpropyl and naphthylmethyl. "Aryl$C_{2-6}$alkenyl" and "aryl$C_{2-6}$alkynyl" should be construed in an analogous fashion.

Typical aryl groups include phenyl and naphthyl. Preferably the aryl is phenyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a novel pharmaceutical composition comprising a compound of formula (I) or a pharmaceutically acceptable salt thereof as defined above and a pharmaceutically acceptable excipient. The skilled person will appreciate that the alternative and preferred embodiments of these pharmaceutical compositions are the alternative and preferred embodiments of the novel compounds of formula (I) provided by the present invention.

Aptly novel compounds of this invention include those wherein $R^2$ and $R^3$ are not 6-position gem-dimethyl.

Aptly novel compounds of this invention include those wherein p is 1 or 2.

Aptly novel compounds of this invention include those wherein $R^1$ is not methyl.

The present invention also provides a process for producing a compound of formula (I) which comprises:

(i) reacting a compound of formula II:

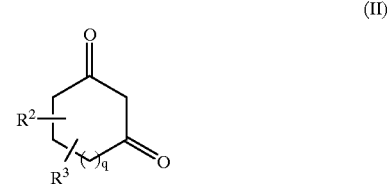

(II)

in which $R^2$, $R^3$ and q are as defined above, with NaH, then reacting with $CS_2$, then with a compound of formula III and then with a compound of formula IV:

$$HalR^1 \quad \text{(III)}$$

$$Hal'CH_2R^{15} \quad \text{(IV)}$$

in which $R^1$ is as defined above, Hal is a halogen atom such as iodine, Hal' is a halogen atom such as bromine or chlorine and $R^{15}$ is $CO_2C_{1-6}$alkyl to produce a compound of formula VI:

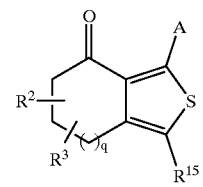

(VI)

in which A is $S(O)_pR^1$, p is zero and $R^1$, $R^2$, $R^3$, $R^{15}$ and q are as defined above and converting the group $R^{15}$ by hydrolysis to a group of formula $CO_2H$ to produce a compound of formula VII:

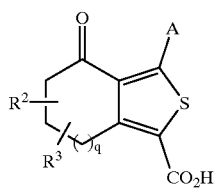

(VII)

in which A is $S(O)_pR^1$, p is zero and $R^1$, $R^2$, $R^3$ and q are as defined above, then reacting with an amine of formula $HNR^4R^5$, where R4 and $R^5$ are as defined above, generally in the presence of an acylation catalyst such as 4-dimethylamino pyridine and a coupling agent such as 1-(3-dimethylaminopropyl)-3-ethylcarbodiimide hydrochloride in a solvent such as DCM for about 18 h to produce the compound of formula I, and (ii) optionally oxidising the compound of formula VI or the compound of formula I thus obtained to a compound of formula VI or I in which p is 1 or 2, for example by using a stoichiometric quantity of mCPBA, generally in a solvent such as $CH_2Cl_2$/dioxan with cooling to about −78° C.; and (iii) optionally converting the compound of formula VI or I, as the case may be, to a compound of formula VI or I in which A is other than $S(O)_pR^1$ by standard techniques.

Further details of the above reactions can be found, for example, in Comprehensive Organic Syntheses, ed. B. M. Trost, Pergamon Press, Oxford.

Compounds of formula I or VI in which A is $SR^1$ can be obtained by reacting a compound of formula I or VI in which A is $S(O)_pR^1$ where p is one or two and $R^1$ is as defined above with a thiol in the presence of a base.

Compounds of formula I or VI in which A is $C_{1-6}$alkyl, $C_{2-6}$alkenyl, $C_{2-6}$alkynyl or $C_{3-6}$cycloalkyl can be obtained by reacting a compound of formula I or VI in which A is $S(O)_pR$ where p is zero or two with an appropriate Grignard reagent.

Compounds of formula I or VI in which A is $OR^1$ can be obtained by reacting a compound of formula I or VI in which A is $S(O)_pR^1$ and p is one or two with an alcohol in the presence of a strong base such as sodium hydroxide.

Compounds of formula I or VI in which A is $NR^1R^{14}$ can be obtained by reacting a compound of formula I or VI in which A is $S(O)_pR^1$ and p is one or two with an amine.

It will be understood that the above transformations of $S(O)_pR^1$ are illustrative and other standard techniques known to the skilled person may alternatively be used.

Compounds of formula VI in which $R^{15}$ is CN, Br or $C(O)CH_3$, p is zero, $R^1$ is $CH_3$ and $R^2$ and $R^3$ are 6,6-dimethyl are commercially available.

Compounds of formulae (II), (III) and (IV) are known in the art or can be made by known methods from known starting materials.

The following Examples illustrate pharmaceutical compositions according to the invention.

| COMPOSITION EXAMPLE 1A Tablets containing 1–25 mg of compound | | | |
|---|---|---|---|
| | Amount mg | | |
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

| COMPOSITION EXAMPLE 1B Tablets containing 26–100 mg of compound | | | |
|---|---|---|---|
| | Amount mg | | |
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| COMPOSITION EXAMPLE 2 Parenteral injection | |
|---|---|
| | Amount |
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

| COMPOSITION EXAMPLE 3 Topical formulation | |
|---|---|
| | Amount |
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human GABA$_A$ receptors containing the α5 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1 β3γ2 cells; 10 nM for α3β3γ2 cells; 10 nM for α5 β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α5 subunit of the human GABA$_A$ receptor of 300 nM or less, preferably of 100 nM or less, and more particularly of 50 nM or less.

The following Examples illustrate the invention:

EXAMPLE 1

6,6-Dimethyl-3-methylthio-1-(pyrrolidin-1-ylcarbonyl)-4,5,6,7-tetrahydrobenzo[c]thiophen-4-one To a stirred solution of 6,6-dimethyl-3-methylthio-4-oxo-4,5,6,7-tetrahydrobenzo[c]thiophene-1-carboxylic acid (1.0 g, 3.7 mmol), 4-dimethylaminopyridine (0.75 g, 6.1 mmol) and 1-(3-dimethylaminopropyl)-3-ethylcarbodiimide hydrochloride (1.15 g, 6 mmol) in DCM (30 mL) was added pyrrolidine (0.34 mL, 4.1 mmol). The mixture was stirred for 18 h then the solution was evaporated and the residue partitioned between EtOAc (20 mL) and water (20 mL). The organic later was separated, washed with 1M HCl (2×20 mL) and sat. K$_2$CO$_3$ (20 ml). The organic layer was separated, dried (MgSO$_4$) and evaporated. The residue was titurated with hexane/ether to afford the title amide (905 mg, 76%) as a colourless solid. mp 153–155° C. C$_{16}$H$_{21}$NO$_2$S$_2$ requires: C, 59.41; H, 6.54; N, 4.33%. Found: C, 59.70; H, 6.73; N, 4.77%. $^1$H NMR (360 MHz, CDCl$_3$) δ 1.05 (6H, s), 1.94–2.04 (4H, m), 2.40 (2H, s), 2.59 (3H, s), 2.84 (2H, s), 3.59–3.62 (4H, m). MS (ES$^+$) 324 (M+1).

EXAMPLE 2

6,6-Dimethyl-1-(dimethylaminocarbonyl)-3-methylthio-4,5,6,7-tetrahydrobenzo[c]thiophen-4-one In the same way as Example 1 using dimethylamine, the title compound (764 mg, 70%) was isolated as a cream solid. mp 135–136° C. C$_{14}$H$_{19}$NO$_2$S$_2$ requires: C, 56.53; H, 6.44; N, 4.71%. Found: C, 56.37; H, 6.31; N, 4.57%. $^1$H NMR (250 MHz, CDCl$_3$) δ 1.05 (6H, s), 2.40 (2H, s), 2.59 (3H, s), 2.67 (2H, s), 3.10 (4H, s). MS (ES$^+$) 298 ((M+1).

EXAMPLE 3

6,6-Dimethyl-1-[(methyl)cyclohexylaminocarbonyl]-3-methylthio-4,5,6,7-tetrahydrobenzo[c]thiophen-4-one In the same was as Example 1 using N-methylcyclohexylamine, the title amide (1.06 g, 78%) was isolated as a colourless solid. mp 161–163° C. C$_{19}$H$_{27}$NO$_2$S$_2$.0.2 (H$_2$O) requires: C, 61.82; H, 7.48; N, 3.79%. Found: C, 61.89; H, 7.41; N, 3.67%. $^1$H NMR (360 MHz, CDCl$_3$) δ 1.08 (6H, s), 1.23–1.40 (2H, m), 1.49–1.90 (8H, m), 2.39 (2H, s), 2.58 (3H, s), 2.64 (2H, s), 2.94 (3H, s), 3.90–4.10 (1H, m). MS (ES$^+$) 366 (M+1).

EXAMPLE 4

6,6-Dimethyl-3-phenylthio-1-(pyrrolidin-1-ylcarbonyl)-4,5,6,7-tetrahydrobenzo[c]thiophen-4-one Step 1: 6,6-Dimethyl-3-methanesulphonyl-1-(pyrrolidin-1-ylcarbonyl)-4,5,6,7-tetrahydrobenzo[c]thiophen-4-one To a stirred solution of 6,6-dimethyl-3-methylthio-1-(pyrrolidin-1-ylcarbonyl)-4,5,6,7-tetrahydrobenzo[c]thiophen-4-one (5.0 g, 16 mmol) in DCM (400 mL) was added meta-chloroperoxybenzoic acid (11.4 g, (70% tech.), 46 mmol) and the mixture stirred at room temperature for 18 h. The solution was washed with Na$_2$CO$_3$ (sat., 3×200 mL), the organic layer separated, dried (Na$_2$SO$_4$) and evaporated. The residue was triturated with ether and the sulphone (4.88 g, 89%) collected by filtration and isolated as a colourless solid. mp 161° C. C$_{16}$H$_{21}$NO$_4$S$_2$ requires: C, 54.06; H, 5.95; N, 3.9%. Found: C, 53.76; H, 5.78; N, 3.89%. $^1$H NMR (250 MHz, CDCl$_3$) δ 1.10 (6H, s), 1.97–2.03 (4H, m), 2.53 (2H, s), 2.90 (2H, s), 3.47–3.78 (7H, m). MS(ES$^+$) 356 (M+1).

Step 2: 6,6-Dimethyl-3-phenylthio-1-(pyrrolidin-1-ylcarbonyl)-4,5,6,7-tetrahydrobenzo[c]thiophen-4-one To a suspension of the sulphone (400 mg, 1.1 mmol) in EtOH (15 mL) was added thiophenol sodium salt (297 mg, 2.2 mmol). The mixture was stirred at room temperature for 3 h then the solvent evaporated. The residue was partitioned between EtOAc (20 mL) and water (30 mL), the organic phase separated, dried (Na$_2$SO$_4$) and evaporated. The resultant oil was triturated with ether/hexane and the colourless solid (330 mg, 76%) collected by filtration. mp 140° C. C$_{21}$H$_{23}$NO$_2$S$_2$ requires: C, 65.42; H, 6.01; N, 3.63%. Found: C, 65.55; H, 5.77; N, 3.98%. $^1$H NMR (360 Hz, CDCl$_3$) δ 1.07 (6H, s), 1.86–1.90 (4H, m), 2.43 (2H, s), 2.78 (2H, s), 3.36–3.60 (4H, m), 7.43–7.51 (3H, m), 7.67–7.70 (2H, m). MS (ES$^+$) 386 (M+1).

EXAMPLE 5

6,6-Dimethyl-3-ethylthio-1-(pyrrolidin-1-ylcarbonyl)-4,5,6,7-tetrahydrobenzo[c]thiophen-4-one In the same way as described in Example 4, Step 2, using ethanethiol sodium salt, the title compound (381 mg, 59%) was isolated as a colourless solid. mp 129–132° C.

$C_{17}H_2NO_2S_2$ requires: C, 60.50; H, 6.87; N, 4.15%. Found: C, 60.74; H, 6.76; N, 3.86%. $^1$H NMR (360 MHz, CDCl$_3$) δ 1.04 (6H, s), 1.47 (3H, t, J=7.5 Hz), 1.94–1.98 (4H, m), 2.40 (2H, s), 2.83 (2H, s), 3.05 (2H, q, J=7.5 Hz), 3.58–3.62 (4H, m). MS (ES$^+$) 338 (M+1).

EXAMPLE 6
6,6-Dimethyl-1-(pyrrolidin-1-ylcarbonyl)-3-(thiazol-2-ylthio)-4,5,6,7-tetrahydrobenzo[c]thiophen-4-one To a suspension of 6,6-dimethyl-3-methanesulphonyl-1-(pyrrolidin-1-ylcarbonyl)-4,5,6,7-tetrahydrobenzo[c]thiophen-4-one (400 mg, 1.1 mmol) in EtOH (10 mL) was added NaOH (1.1 mL of a 3 M solution, 3.3 mmol) followed by 2-mercaptothiazole (0.39 g, 3.3 mmol). The mixture was heated at 70° C. for 5 h then the solution was evaporated. The residue was partitioned between EtOAc (20 mL) and NaOH (1 M; 30 mL). The organic phase was separated, dried (Na$_2$SO$_4$) and evaporated. The residue was chromatographed on silica gel, eluting with EtOAc:hexane (2:1), to afford the title compound (120 mg. 28%) as a colourless solid. $^1$H NMR (250 MHz, CDCl$_3$) δ 1.07 (6H, s), 1.90–1.95 (4H, m), 2.45 (2H, s), 2.83 (2H, s), 3.40–3.62 (4H, m), 7.55 (1H, d, J=3.4 Hz), 7.97 (1H, d, J=3.4 Hz). MS (ES$^+$) 393 (M+1).

EXAMPLE 7
6,6-Dimethyl-1-(homopiperidin-1-ylcarbonyl)-3-methylthio-4,5,6,7-tetrahydrobenzo[c]thiophen-4-one In the same was as described in Example 1 using hexamethyleneimine the title compound (1.0 g, 85%) was isolated as a colourless solid. mp 168–170° C. $C_{18}H_{25}NO_2S_2$ requires: C, 61.50; H, 7.17; N, 3.98%. Found: C, 61.81; H, 7.17; N, 3.83%. $^1$H NMR (360 MHz, CDCl$_3$) δ 1.04 (6H, s), 1.58–1.68 (4H, m), 1.70–1.80 (4H, m), 2.39 (2H, s), 2.58 (3H, s), 2.67 (2H, s), 3.56–3.65 (4H, m). MS (ES$^+$) 352 (M+1).

EXAMPLE 8
6,6-Dimethyl-1-(pyrrolidin-1-ylcarbonyl)-3-(2,2,2-trifluoroethylthio)-4,5,6,7-tetrahydrobenzo[c]thiophen-4-one To a suspension of 6,6-dimethyl-3-methanesulphonyl-1-(pyrrolidin-1-ylcarbonyl)-4,5,6,7-tetrahydrobenzo[c]thiophen-4-one (400 mg, 1.1 mmol) in EtOH (15 mL) was added NaOH (0.7 mL of a 3 M solution, 2.3 mmol) followed by 2,2,2-trifluoroethanethiol (0.2 mL, 2.2 mmol). The mixture was stirred at room temperature for 3 h then evaporated. The residue was partitioned between EtOAc (20 mL) and NaOH (1M; 30 mL). The organic layer was separated, dried (Na$_2$SO$_4$) and evaporated. The residue was triturated with ether and the colourless solid (166 mg, 35%) collected by filtration. $C_{17}H_{20}F_3NO_2S_2$ requires: C, 52.16; H, 5.15; N, 3.58%. Found: C, 51.86; H, 4.99; N, 3.61%. $^1$H NMR (360 MHz, CDCl$_3$) δ 1.05 (6H, s), 1.95–1.99 (4H, m), 2.42 (2H, s), 2.86 (2H, s), 3.57–3.63 (4H, m), 3.66 (2H, q, J=9.5 Hz). MS (ES$^+$) 392 (M+1).

EXAMPLE 9
6,6-Dimethyl-3-isopropylthio-1-(pyrrolidin-1-ylcarbonyl)-4,5,6,7-tetrahydrobenzo[c]thiophen-4-one In the same way as that described in Example 8, using 2-propanethiol, the title compound (175 mg, 44%) was isolated as a colourless solid. $C_{18}H_{25}NO_2S_2$ requires: C, 61.50; H, 7.17; N, 3.98%. Found: C, 61.42; H, 7.12; N, 3.92%. $^1$H NMR (250 MHz, CDCl$_3$) δ 1.04 (6H, s), 1.48 (6H, d, J=6.6 Hz), 1.93–1.99 (4H, m), 2.40 (2H, s), 2.82 (2H, s), 3.49 (1H, septet, J=6.6 Hz), 3.59–3.65 (4H, m). MS (ES$^+$) 352 (M+1).

EXAMPLE 10
6,6-Dimethyl-3-phenyloxy-1-(pyrrolidin-1-ylcarbonyl)-4,5,6,7-tetrahydrobenzo[c]thiophen-4-one In the same way as that described in Example 8, using phenol, the title compound (360 mg, 69%) was isolated as a colourless solid. $^1$H NMR (360 MHz, CDCl$_3$) δ 1.08 (6H, s), 1.90–1.93 (4H, m), 2.40 (2H, s), 2.84 (2H, s), 3.50–3.60 (4H, s), 7.20–7.30 (3H, m), 7.39–7.45 (2H, m). MS (ES$^+$) 370 (M+1).

EXAMPLE 11
6,6-Dimethyl-3-methylthio-1-(morpholin-4-ylcarbonyl)-4,5,6,7-tetrahydrobenzo[c]thiophen-4-one In the same way as that described in Example 1, using morpholine, the title amide (1.1 g, 87%) was isolated as a colourless solid. mp 168–169° C. $C_{16}H_{21}NO_3S_2$ requires: C, 56.61; H, 6.24; 6.24; N, 4.13%. Found: C, 56.73; H, 6.06; N, 4.01%. $^1$H NMR (360 MHz, CDCl$_3$), δ 1.05 (6H, s), 2.40 (2H, s), 2.59 (3H, s), 2.67 (2H, s), 3.64–3.67 (4H, m), 3.71–3.74 (4H, m). MS (ES$^+$) 340 (M+1).

EXAMPLE 12
6,6-Dimethyl-1-(4-methylpiperazin-1-ylcarbonyl)-3-methylthio-4,5,6,7-tetrahydrobenzo[c]thiophen-4-one In the same way as that described in Example 1, using N-methylpiperazine, the title compound (0.5g, 39%) was isolated as a colourless solid. mp 123–125° C. $C_{17}H_{24}N_2O_2S_2$ requires: C, 57.92; H, 6.86; N, 7.95%. Found: C, 58.12; H, 6.94; N, 7.84%. $^1$H NMR (250 MHz, CDCl$_3$) δ 1.05 (6H, s), 2.33 (3H, s), 2.40 (2H, s), 2.41–2.46 (4H, m), 2.59 (3H, s), 2.66 (2H, s), 3.64–3.68 (4H, m). MS (ES$^+$) 353 (M+1).

We claim:

1. A compound of formula (I) or a pharmaceutically acceptable salt thereof:

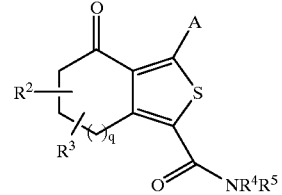

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^6$;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, each of which rings is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ and $R^5$ are individually hydrogen, $C_{1-6}$alkyl, $C_{2-6}$alkenyl, $C_{2-6}$alkynyl or $C_{3-8}$cycloalkyl or $R^4$ and $R^5$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^6$ is hydrogen or $C_{1-6}$alkyl;

p is zero, 1 or 2; and q is 0, 1 or 2.

2. A compound according to claim 1 where A is $S(O)_p R^1$.

3. A compound according to claim 1 wherein $R^1$ is $C_{1-6}$alkyl, $C_{2-6}$alkenyl or $C_{3-6}$ cycloalkenyl each of which is optionally substituted by amino, di($C_{1-6}$alkyl)amino, hydroxy, $C_{1-6}$alkoxy, $C_{1-6}$alkylaminocarbonyl or one, two or three halogen atoms; aryl or aryl$C_{1-6}$alkyl optionally substituted on the aryl ring by halogen, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, which ring is optionally substituted by halogen, $C_{1-6}$alkoxy, $C_{1-6}$alkylthio, aryl or $C_{1-6}$alkyl.

4. A compound according to claim 1 wherein $R^2$ and $R^3$ are both methyl.

5. A compound according to claim 1 wherein:

A is $S(O)_p R^1$ or $OR^1$;

$R^1$ is $C_{1-6}$alkyl optionally substituted by one, two or three fluorine atoms, phenyl optionally substituted by fluorine or chlorine, or thiazole optionally substituted by $C_{1-4}$alkyl or fluorine;

$R^2$ and $R^3$ are methyl;

$R^4$ and $R^5$ are independently hydrogen, methyl or cyclohexyl or $R^4$ and $R^5$ together with the nitrogen atom to which they are attached form a piperidine, piperazine, hexamethyleneimine or morpholine ring, the further nitrogen atom in the piperazine ring being optionally substituted by methyl;

p is zero or two; and q is one.

6. A pharmaceutical composition comprising a compound according to claim 1 or a pharmaceutically acceptable salt thereof and a pharmaceutically acceptable excipient.

7. A method of treatment or prevention of a condition which requires the administration of a cognition enhancing agent which comprises administering to a subject suffering from or prone to such a condition a therapeutically or prophylactically effective amount of a compound according to claim 1 or a pharmaceutically acceptable salt thereof.

* * * * *